(12) United States Patent
Fillmore

(10) Patent No.: US 10,325,064 B2
(45) Date of Patent: Jun. 18, 2019

(54) PATIENT READMISSION PREDICTION TOOL

(71) Applicant: 3M INNOVATIVE PROPERTIES COMPANY, St. Paul, MN (US)

(72) Inventor: Herb Fillmore, Blauvelt, NY (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 522 days.

(21) Appl. No.: 13/744,502

(22) Filed: Jan. 18, 2013

(65) Prior Publication Data

US 2013/0191158 A1  Jul. 25, 2013

Related U.S. Application Data

(60) Provisional application No. 61/588,712, filed on Jan. 20, 2012.

(51) Int. Cl.
   *G06F 19/00* (2018.01)
   *G16H 50/30* (2018.01)
   *G16H 50/50* (2018.01)

(52) U.S. Cl.
   CPC .............. *G06F 19/00* (2013.01); *G16H 50/30* (2018.01); *G16H 50/50* (2018.01)

(58) Field of Classification Search
   CPC ........ G06Q 40/08; G06Q 50/24; G06Q 50/22; G06F 19/34; G06F 19/3431; G06F 19/3437; G06N 5/02; G06N 99/005
   USPC ........................................................ 705/2–3
   See application file for complete search history.

(56) References Cited

U.S. PATENT DOCUMENTS

| | | | |
|---|---|---|---|
| 2001/0039503 A1* | 11/2001 | Chan ..................... | G06F 19/325 705/2 |
| 2002/0072933 A1* | 6/2002 | Vonk .................... | A61B 5/0002 705/2 |
| 2011/0295622 A1* | 12/2011 | Farooq .................. | G06Q 10/10 705/3 |

(Continued)

OTHER PUBLICATIONS

Yuan et al , "Model selection and estimation in regression with grouped variables," Feb. 2006, Journal of the Royal Statistical Society: Series B (Statistical Methodology); vol. 68 Issue 1, p. 49-67. 19p.*

(Continued)

*Primary Examiner* — Michael Tomaszewski
(74) *Attorney, Agent, or Firm* — X. Christina Huang

(57) ABSTRACT

Facilities are provider herein for predicting potentially preventable patient readmissions after discharge from a health care provider. A patient readmission prediction model is built based on received patient data for one or more health care providers. Patient attributes discernible from that patient data are extracted and analyzed, and certain attributes are selected as being meaningful in predicting likelihood of post-discharge, potentially preventable patient readmission by patients newly admitted to a health care provider. Patient data for a newly admitted patient is obtained, and the readmission prediction model is applied against that patient data for the newly admitted patient to obtain a predictive risk score that is indicative of the likelihood that the newly admitted patient will experience a potentially preventable readmission post-discharge from the health care provider.

18 Claims, 8 Drawing Sheets

(56) References Cited

U.S. PATENT DOCUMENTS

2011/0313788 A1* 12/2011 Amland ................ G06Q 50/22
                                                                   705/3
2012/0065987 A1*  3/2012 Farooq et al. .................... 705/2
2013/0024124 A1*  1/2013 Collazo ................ G16H 50/30
                                                                  702/19

OTHER PUBLICATIONS

Jmp, A., and Marcel Proust. "Multivariate Methods." (2010). p. 121.*
Kansagara et al., Risk Prediction Models for Hospital Readmission, A Systematic Review, Clinical Review, Oct. 19, 2011, pp. 1688-1698, JAMA, vol. 306, No. 15.

* cited by examiner

| | | |
|---|---|---|
| TREND | | 6.5% |
| BASELINE MEDICAL SPEND PM / PM | $ | 326.13 |
| AVERAGE MEMBER MONTHS | | 42,054 |
| DISTINCT MEMBERS | | 44,850 |

2009 HCO MEMBERS IN PRIMARY SERVICE AREA

| | | YEAR0 | YEAR1 PMPM | YEAR2 PMPM | YEAR3 PMPM | YEAR4 PMPM | YEAR5 PMPM |
|---|---|---|---|---|---|---|---|
| MODEL WITH NO FOCUS ON PREVENTABLES | | | | | | | |
| MEDICAL SPEND PMPM | 100.00% | $ 326.13 | $ 347.33 | $ 369.91 | $ 393.95 | $ 419.56 | $ 446.83 |
| TREND | | | 6.5% | 6.5% | 6.5% | 6.5% | 6.5% |
| TOTAL COST | | $ 164,581,413 | $ 175,279,205 | $ 186,627,353 | $ 198,806,056 | $ 211,728,450 | $ 225,490,799 |
| MODEL WITH FOCUS ON PREVENTABLES | | | | | | | |
| PREVENTABLES | | | | | | | |
| PPA | | $ 3.92 | $ 0.42 | $ 0.53 | $ 0.66 | $ 0.79 | $ 0.92 |
| PPR | | $ 1.81 | $ 0.39 | $ 0.46 | $ 0.54 | $ 0.62 | $ 0.70 |
| PPV | | $ 5.21 | $ 0.28 | $ 0.59 | $ 0.93 | $ 1.30 | $ 1.69 |
| PPS | | $ 74.95 | $ 2.39 | $ 5.10 | $ 8.06 | $ 11.25 | $ 14.58 |
| PREVENTABLES TOTAL PMPM | | $ 85.89 | $ 3.48 | $ 6.68 | $ 10.19 | $ 13.96 | $ 17.89 |
| REALLOCATION OF SERVICES AND CARE MNGT FEE PMPM | 26.34% | | $ 3.13 | $ 3.19 | $ 3.25 | $ 3.31 | $ 3.37 |
| MEDICAL SPEND PMPM | 100.00% | $ 326.13 | $ 346.99 | $ 366.05 | $ 382.90 | $ 397.14 | $ 408.44 |
| TREND | | | 6.4% | 5.5% | 4.6% | 3.7% | 2.8% |
| TOTAL COST | | $ 164,581,413 | $ 175,105,060 | $ 184,725,530 | $ 193,228,330 | $ 200,416,134 | $ 206,116,502 |
| SAVINGS | | | $ 174,145 | $ 1,916,823 | $ 5,577,728 | $ 11,312,315 | $ 19,374,297 |
| CUMULATIVE SAVINGS | | | $ 174,145 | $ 2,120,968 | $ 7,698,694 | $ 19,011,010 | $ 38,385,307 |

FIG. 1

PATIENT READMISSION PREDICTION TOOL

CROSS-REFERENCE TO RELATED APPLICATIONS

This application claims the benefit of U.S. Provisional Patent Application No. 61/588,712, filed Jan. 20, 2012, the entirety of which is herein incorporated by reference.

TECHNICAL FIELD

This invention relates to predicting and preventing potentially preventable readmissions of health care patients of health care providers.

BACKGROUND OF INVENTION

Cost of patient care is an increasingly important consideration for health care providers. A health care provider refers generally to any provider or facilitator of health care services, and can encompass a broad range of entities, such as physician and/or non-physician health care practitioners, physician groups, facilities, health systems, and/or health care organizations, such as accountable care organizations, as examples. Identifying areas for potential savings benefits health care providers looking to cut costs. Cost cutting is a significant motivator for providers who are engaged in performance-based payment schemes, such as capitation or value-based purchasing. Accountable Care Organizations and Person Centered Medical Homes are more recent examples of value-based purchasing, where providers of care are paid on the basis of meeting certain quality targets and reducing costs of care. Accordingly, cost-cutting through the identification of areas for potential cost savings is an important task for health care providers.

BRIEF SUMMARY OF THE INVENTION

The shortcomings of the prior art are overcome and additional advantages are provided through the provision of a method which includes, for instance, obtaining a patient readmission prediction model, the patient readmission prediction model based on a determination of patient attributes selected as being meaningful in predicting likelihood of post-discharge, potentially preventable patient readmission; and predicting, for a patient admitted for care by a health care provider, likelihood of a potentially preventable readmission of the patient post-discharge from the health care provider, the predicting comprising applying the obtained patient readmission prediction model against patient data for the admitted patient to obtain a predictive risk score indicative of the probability of a potentially preventable readmission of the patient post-discharge from the health care provider.

Further, a system is provided which includes a memory; and a processor, in communication with the memory, wherein the system is configured to perform, for instance: obtaining a patient readmission prediction model, the patient readmission prediction model based on a determination of patient attributes selected as being meaningful in predicting likelihood of post-discharge, potentially preventable patient readmission; and predicting, for a patient admitted for care by a health care provider, likelihood of a potentially preventable readmission of the patient post-discharge from the health care provider, the predicting comprising applying the obtained patient readmission prediction model against patient data for the admitted patient to obtain a predictive risk score indicative of the probability of a potentially preventable readmission of the patient post-discharge from the health care provider.

Yet further, a computer program product is provided which includes a tangible storage medium readable by a processor and storing instructions for execution by the processor to perform a method which includes, for instance: obtaining a patient readmission prediction model, the patient readmission prediction model based on a determination of patient attributes selected as being meaningful in predicting likelihood of post-discharge, potentially preventable patient readmission; and predicting, for a patient admitted for care by a health care provider, likelihood of a potentially preventable readmission of the patient post-discharge from the health care provider, the predicting comprising applying the obtained patient readmission prediction model against patient data for the admitted patient to obtain a predictive risk score indicative of the probability of a potentially preventable readmission of the patient post-discharge from the health care provider.

Additional features and advantages are realized through the concepts of the present invention. Other embodiments and aspects of the invention are described in detail herein and are considered a part of the claimed invention.

BRIEF DESCRIPTION OF THE DRAWINGS

One or more aspects of the present invention and other objects, features, and advantages of the invention are apparent from the following detailed description taken in conjunction with the accompanying drawings in which:

FIG. 1 provides an example depiction of the impact of reduction in potentially preventable events on total cost-of-care over a time period;

DETAILED DESCRIPTION

Figure 2:
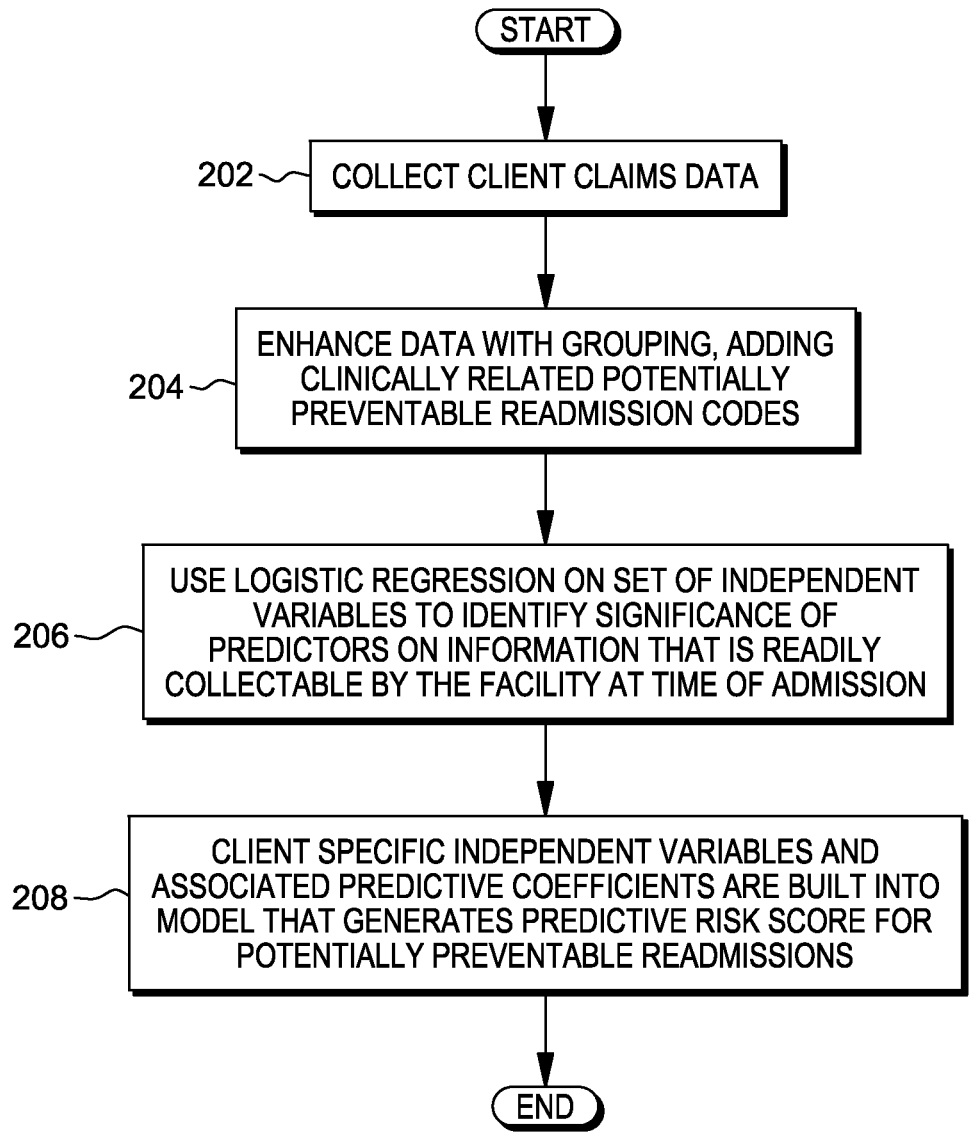
FIG. 2 depicts one example process for building a patient readmission prediction model, in accordance with one or more aspects of the present invention.

An accountable care arrangement, which is just one example of value-based purchasing, is a contractual structure designed to help manage total cost-of-care of the health care organizations (comprising health care providers) that form the Accountable Care Organization. Total cost-of-care represents the expense incurred by an Accountable Care Organization for covered health care services provided to members attributed to the health care organizations of the Accountable Care Organization.

Accountable care arrangements are designed to leverage key health care organization competencies while also aligning incentives between payer and provider. Nationally, many payers and providers are realizing the need to collaborate to 'bend the cost curve' and bring annual health care cost increases closer to the rate of inflation Innovative payers and providers, through accountable care arrangements, are partnering to identify areas for increasing value where costs can be lowered and outcomes improved.

One way overall cost-of-care can be reduced is by appropriately identifying and managing potentially preventable events. Potentially preventable events are healthcare events/ services that may be unnecessary, avoidable, and, if properly managed, may produce lower overall cost-of-care and improved health outcomes. Understanding the volume of these services and system variation in the delivery of these services assists in the development and management of programs that reduce overall cost-of-care, while improving the quality of that care for patients. In a cost-of-care analysis and identification of potentially preventable events, a breakdown of the distribution of potentially preventable events by aggregated health status category can be determined. There are many methods for classifying health status, for example persons with one chronic condition, persons with multiple chronic conditions, healthy patients, etc. After choosing a health status taxonomy that classifies and identifies the costs and health risks inherent in a patient population, the breakdown of potentially preventable events can be provided in the form of a chart that shows the distribution of the money spent on potentially preventable events.

Segmenting the population through the use of health status groups can provide a meaningful and actionable list of individuals for whom potentially preventable events could be reduced through programs such as targeted case management. Small, incremental reductions in potentially preventable events can have a material impact on total cost-of-care over a specified time period.

FIG. 1 provides an example depiction of the impact of reduction in potentially preventable events on total cost-of-care over a time period. Model 100 of FIG. 1 demonstrates the impact of a moderate reduction in potentially preventable events over a five-year term. It compares total cost-of-care if trend is left unimpeded for five years at 6.5% ("Model with no focus on preventables") to total cost-of-care where trend is reduced through an iterative reduction in potentially preventable events over the same five-year period ("Model with focus on preventables"). In this example, the total cost-of-care by year five under the model with no focus on preventables is a $446.83 Per-Member, Per-Month (PMPM), whereas the total cost-of-care by year five under the model with a focus on preventables is a $408.44 Per-Member, Per-Month (PMPM). The net result is a $38 Per-Member, Per-Month difference in total cost-of-care by year five ($446.83 vs. $408.44), a total cumulative savings after five years of $38 million, and a trend that is reduced to 2.8%.

The model of FIG. 1 recognizes that investments will likely be required in alternate levels of care and/or care management. However, there are several types of potentially preventable events, including patient readmissions that may be preventable (i.e. "potentially preventable readmissions", also referred to herein as simply "preventable readmissions"). Potentially preventable readmissions represent a modest share of total preventable dollars, but interventions to improve readmission rates can be effected, provided that the right patients are identified for the intervention. Thus, potentially preventable readmissions are an example of events that may be highlighted within certain health status groups and targeted for intervention.

Patient readmissions can be both a quality indicator and a large source of avoidable costs, and are, in accordance with aspects of the present invention, of heightened interest in an age of value-based purchasing. Thus, one area ripe for improving outcomes and cost cutting is identification and prevention of preventable patient readmissions, and what is needed is an effective tool for identifying and prioritizing preventable readmission of patients.

In accordance with aspects of the present invention, a patient readmission prediction tool is provided for facilitating identification and prioritization of patients who are at relatively high risk of having a potentially preventable readmission. The readmission prediction tool utilizes a model that identifies characteristics of patients that are important for indicating likelihood that a patient, for reasons clinically predating the present admission, will be readmitted to a provider after discharge. Patient information, such as claims information, is examined across a variety of patient attributes and indicators. The most significant attributes are selected, and the result is a model which is calibrated to at least one health care provider's particular setting (for instance region or health care system) in which the patient is being served, by way of administrative data (for instance data from claims associated with a particular institution) and, based on a derivation of variables from that claims data and coefficients (weights) associated with those variables. These are used to predict readmission probability for incoming, that is newly admitted, patients. The calibration of the model to the provider setting facilitates improvement in the prediction of preventable readmissions of patients of the provider or providers associated with that setting (such as within that geographic area). Accordingly, the model identifies patient attributes that can predict a patient's likelihood to have a preventable readmission, and the model is calibrated for a particular institution from which the patient data is received. The model can be applied against data for newly admitted patients to score the patients in terms of the probability of a preventable readmission following discharge. The tool provides cost identification and elimination applications.

Aspects of the present invention facilitate predicting probability of readmission for newly admitted patients ("New Admits") based on patient data from previously admitted patients (e.g., those known to the hospital or other care provider establishment), and further facilitate prioritizing the New Admits for receiving care management intervention, or other services. In one example, the prediction is made for New Admits the morning after they are admitted for care to a health care provider, and made using data for patient attributes considered to be significant predictors of potential readmission. These patient attributes correlate to selected variables of the readmission prediction model, and for which patient data for the New Admits is available. A non-limiting list of possible patient attributes include one or more of: number and/or occurrence of discharge(s) within the last n number of months (such as 12 months, in one example), with diagnoses and dates; length of stay of previous patient admission(s); patient age; patient gender; patient race; geographic location, such as Zip code, county, etc of the patient and/or provider; socio-economic status of the patient; number and/or occurrence of previous patient admissions and/or readmissions; occurrence and/or frequency of patient emergency room and/or intensive care unit use within a given time period; payer for the patient, diagnosis of current patient admission, source of patient admission, length of stay of last patient admission, the occurrence of patient admission within a past period of time, clinical lab values (such as recent clinical lab values), or patient social characteristics. Additionally or alternatively, the patient attributes can include one or more of: patient diagnostic conditions, patient morbidity characteristics, patient history of disease categories, such as congestive heart failure, chronic obstructive pulmonary disease, advanced liver disease, diabetes with complication, severe chronic renal failure, Parkinson's disease, leukemia, substance abuse, bipolar conditions, and/or severe personality disorder.

Some patient attributes, such as those listed above, predate the current admission, and thus the readmission prediction tool is based, at least partially, on "priors". One advantage provided by this is that it facilitates immediate determination of a predictive risk score indicative of the probability of a potentially preventable readmission, and allows for timely care management interventions with even the shortest stay newly admitted patients. In other words, even a patient who may only have a two-day stay with the provider to which the patient is admitted can be scored before discharge, and the care management staff can act on that score. In one example, data for the variables used in the model (i.e. patient data for newly admitted patients) can be obtained electronically the day after admission, for instance, and used in predicting likelihood of patient readmission of the admitted patients.

FIG. 2 depicts one example process for building a patient readmission prediction model for use in predicting potentially preventable patient readmission, in accordance with one or more aspects of the present invention. In the example of FIG. 2, the model is built based on patient data for a patient pool of at least one health care provider. For instance, the patient pool may be the patient pool for a client hospital or health care organization that encompasses multiple physician practices having multiple sets of attributed members.

The process of FIG. 2 begins with collection of client claims data for health care claims spanning a period of time (202). For instance, the past two years of patient claims data is obtained for patients of the client. It should be understood that the period of time could be shorter or longer than two years. The patient claims data could alternatively or additionally be data obtained across a particular geographic area, for instance for an entire state that makes available historic claims files provided to a regional payer, or at the state or federal level.

Next, the obtained data is enhanced by grouping (204)— in this case, the addition of clinically related potentially preventable readmission codes that identify and categorize the claims according to the degree to which each claim is considered a potentially preventable readmission (204). In one example, the data is enhanced through the use of Potentially Preventable Readmission (PPR) Grouping Software, offered by 3M® Health Information Systems (Salt Lake City, Utah, United States of America), and the data enhancement adds Clinically Related PPR Codes to the data. In other examples, the data can be enhanced/grouped according to a different scheme that identifies which claims include readmissions that were potentially preventable. As part of this grouping and enhancement, patient attributes are identified based on the diagnosis codes and interactions of combinations of patient attributes for determining significant predictors of readmission.

The identified patient attributes constitute variables that may or may not be significant for predicting readmission likelihood. Statistical analysis is performed on the identified attributes to identify which attributes are significant. Thus, a logistic regression, as is known by those having ordinary skill in the art, is run on the identified variables in order to identify the significance of the variables in the chosen setting as predictors of readmission (206). These variables can include those patient attributes identified above, for instance. In one example, a review is performed of the modeling variables (such as those above) in contingency tables, which are, in one example, tables that display levels of variable values and their association with outcomes of interest singly and in combination with other variables. The review can identify a priori candidates for inclusion in the model. Then, variables that showed strong promise (in terms of their significance) in contingency tables, or were known to have clinical relevance, were entered into stepwise regression modeling. Stepwise regression modeling is a standard statistical process that automatically enters variables one by one into a model, testing the resulting power of the model and significance of the variable. Standards are established for considering a variable's entry into the model, and these are known as significance level for elimination (SLE) in the model, and for significance level for selection (SLS) in the model. In one example, an SLE of 0.15 statistical significance and SLS of 0.10 is used, however these values may vary depending on the significances desired. In one approach, values that are scientifically acceptable and result in a broader pool of candidate variables than more restrictive assumptions are chosen, allowing for the possibility of more robust models that can reflect the complexities of real world applications.

A result of the regression is a set of client-specific variables and associated coefficients for the variables, calibrated for the particular client institution, such as a hospital or health care organization. The coefficients indicate the level of significance a particular variable plays in indicating probability of a readmission that is preventable. For instance, it might be determined that the age of a patient and length of stay of the patient are the most important variables in determining a patient's probability of readmission, while race may be important, but not nearly as significant.

The variables and coefficients are built into an equation of a readmission prediction model (208) that is executed against New Admit patient data to score newly admitted patients for readmissions likelihood. This is described in further detail below. The equation is, in one example, of the form $C_1X_1+C_2X_2+\ldots+C_NX_N=PRS$, where $X_i$ represents a patient attribute variable, $C_i$ represents the coefficient of that variable, and PRS represents the predictive risk score for that patient when patient data for each variable $X_i$ is input into the equation.

The predictive risk score is based on factors that are associated with readmissions that might be prevented. Scores that include predictions for admissions that cannot be prevented may be less useful for providers hoping to intervene in the course of events. If an admission is not potentially preventable, then, by definition, there is little that can be done to prevent the readmission, and efforts on prevention expended in that direction are likely to be less useful than if the resources were directed elsewhere. If a patient is identified as being at high risk for readmissions but those readmissions are generally not preventable, then the patient may still need care but of a different type. Thus, the identification of preventable readmissions allows the provider to uncover systemic issues and propose systemic solutions to problems that are associated with readmissions, while, in some cases, the non-preventable readmissions that are easily predicted become an issue of resource planning.

Factors that make a readmission not potentially preventable include the discharge status of a prior discharge of the patient; for example, patients who leave against medical advice (AMA), or patients who are transferred to another acute care hospital, can have readmissions that are not considered potentially preventable. The type of prior discharge can also make a readmission not potentially preventable—for example, discharges in which follow-up care is intrinsically complex and extensive. This category includes diagnoses such as metastatic malignancies, multiple traumas, and burns. A long time interval between discharge and readmission, such as greater than 30 days, can reduce the confidence level that readmission is causally linked to the prior discharge.

Figure 3:
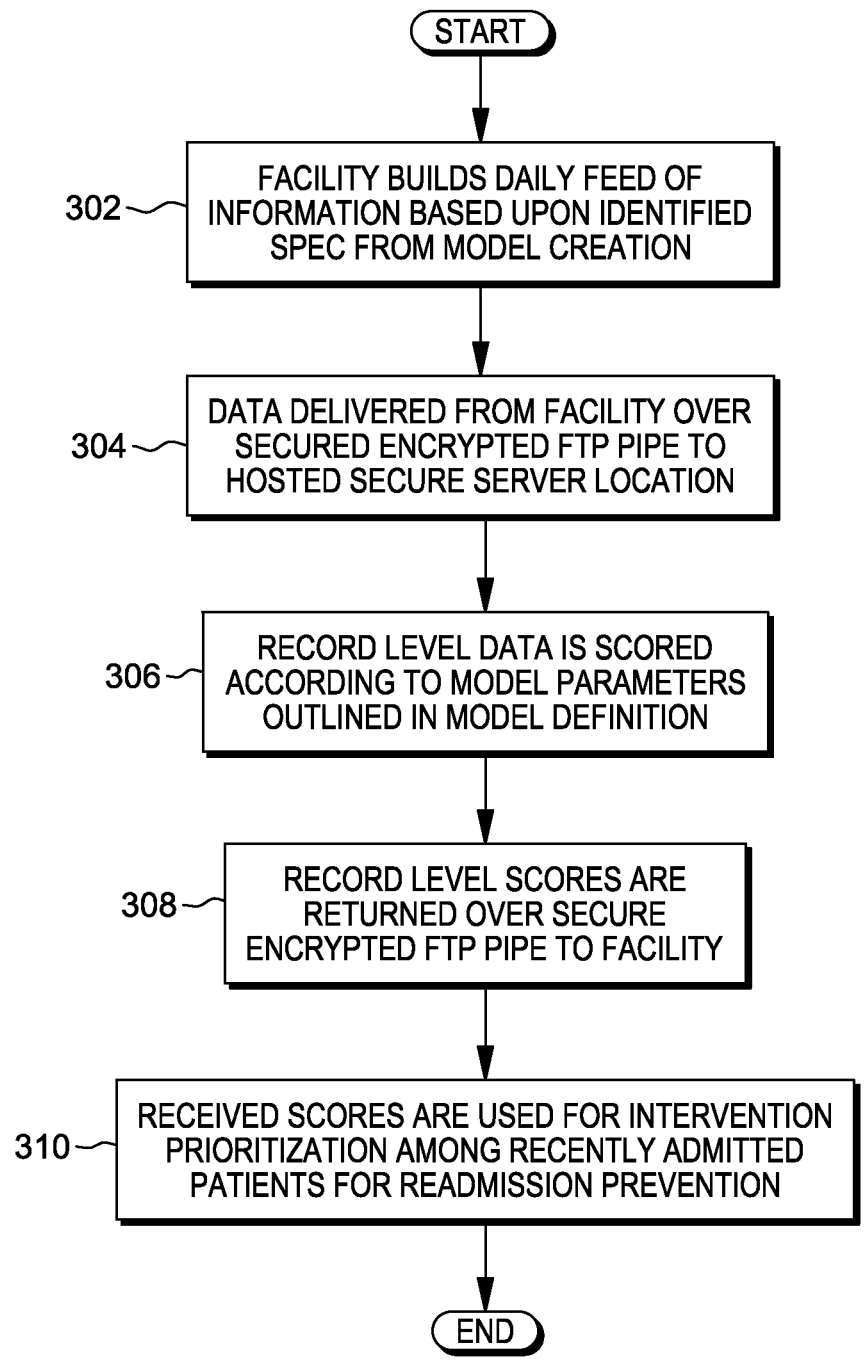
FIG. 3 depicts an example process for executing a built readmission prediction model, in accordance with one or more aspects of the present invention.

FIG. 3 depicts an example process for executing a built readmission prediction model, in accordance with one or more aspects of the present invention. The process begins with a facility, such as a client hospital or other institution, periodically building a data feed based on a specification identified from the model creation described above (302). When a readmission prediction model is built, a specification of the useful variables (e.g. those included in the equation) can be provided to the facility so that the facility can build its data feed to include patient data for those variables. In this manner, the data provided by the facility can be tailored specifically to what is needed to run the model. The facility can aggregate, on a periodic basis, patient data and information for some or all of the variables identified by the regression model as being useful. This patient data and information is for newly admitted patients (e.g. those admitted during that day, or those admitted the previous day, as examples). This data can then be provided to a model execution server, for instance over a secured/encrypted file transfer protocol (FTP) pipe to a secure server location (304). The model execution server can score, on a record-level (i.e. patient by patient), the predicted risk of readmission according to the model parameters (e.g. variables and coefficients in the build readmission prediction model) (306).

One result of this scoring is a Predictive Risk Score ("Risk Score") for the potentially preventable readmissions of each newly admitted patient. In one example, the Risk Score ranges from 0 to 1, indicating the probability of a potentially preventable readmission for a patient. An average probability for a particular hospital might be about 0.22 (22%). In that case, a patient Risk Score higher than 0.22 indicates a higher probability for a potentially preventable readmission of the patient, while a lower patient Risk Score indicates a lower probability for a potentially preventable readmission of the patient. In other words, a higher Risk Score for a newly admitted patient indicates a higher likelihood that the patient will experience a potentially preventable readmission after discharge. The Risk Score can be useful to the health care provider for many purposes. Example purposes include, but are not limited to: discharge management, follow-up activity, and clinical decision making.

Continuing with FIG. 3, the record level scores are returned to the facility over a secure encrypted FTP pipe (308) and used for, in this example, intervention prioritization among the recently admitted patients, to facilitate preventing readmission by at least some of the newly admitted patients (310).

Figure 4:
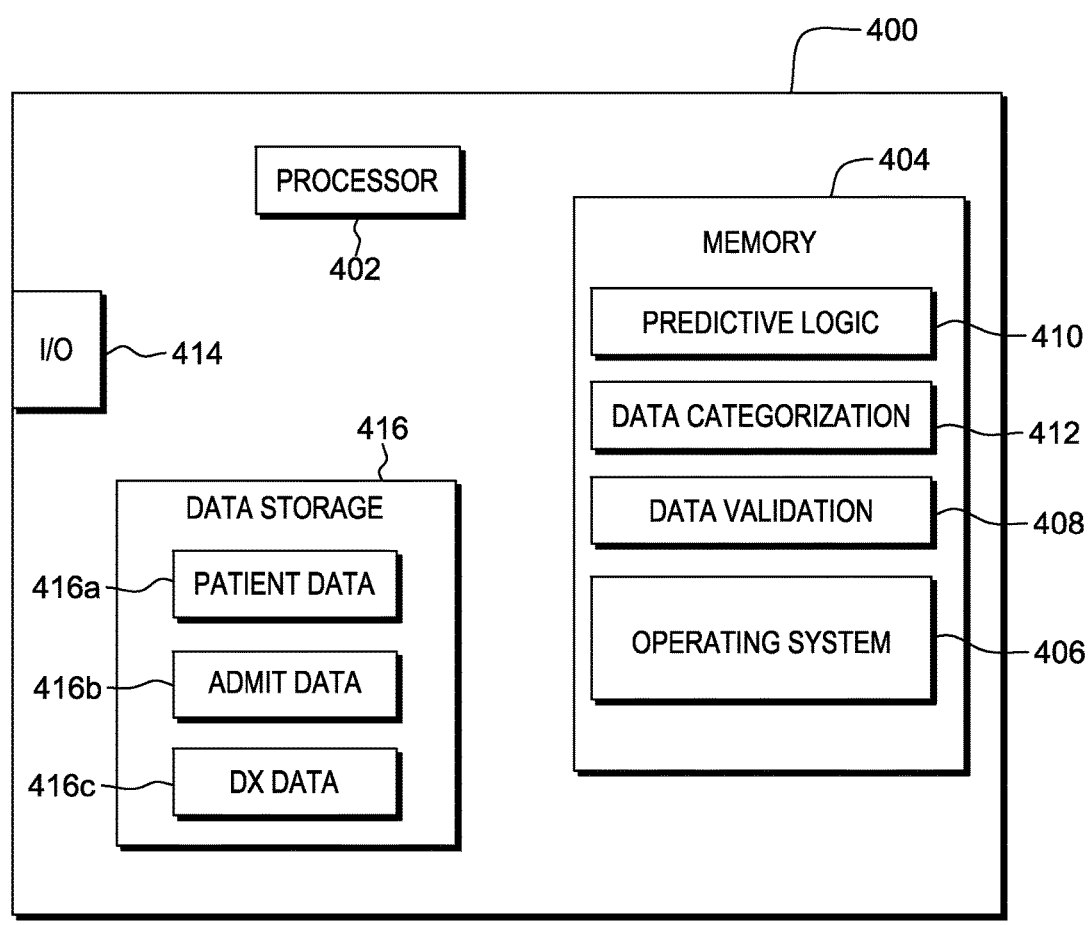
FIG. 4 depicts one example of a system to incorporate and use one or more aspects of the present invention.

FIG. 4 depicts one example of a system to incorporate and use one or more aspects of the present invention. In one example, system 400 encompasses a model execution server for facilitating performance of model execution described above with reference to FIG. 3, for instance by applying a built model against received newly admitted patient data. In other examples, system 400 may additionally or alternatively build the model, as described below with reference to FIG. 6. System 400 is suitable for storing and/or executing program code, such as program code for performing processes described herein, and includes at least one processor 402 coupled directly or indirectly to memory 404 (e.g. through a bus, not depicted). In operation, processor(s) 402 obtain from memory 404 one or more instructions for execution by the processors. A non-limiting list of examples of memory 404 includes a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Memory 404 includes an operating system 406 and one or more software facilities 408, 410, 412 for performing additional aspects of the present invention, described below.

Input/Output (I/O) controllers 414 facilitate input and output of data, such as input and output from/to peripheral devices (keyboards, pointing devices, displays, printers, etc.). I/O 414 can include one or more network adapters to enable system 400 to become coupled to other systems through intervening private or public networks. Modems, cable modems and Ethernet cards are just a few of the available types of network adapters. In one example, the network adapter(s) facilitate obtaining patient data (such as health care claims data) from health care provider(s) or other sources, as well as other data, from remote sources, to facilitate aspects of the present invention.

Source patient data can be received by system 400 via I/O 414 and stored in data storage 416. Data storage 416 includes one or more of non-volatile storage devices, such as magnetic disk drives, optical disk drives, tape drives, etc.), and may include an internal storage device or an attached or network-accessible storage. Computer programs in storage 416 may be loaded into memory 404 and executed by a processor 402 in a manner known in the art.

Source data includes, in one example, daily admissions data from a facility such as a hospital. In one particular embodiment, admissions data for a given day is transferred to system 400 the following morning for execution of the readmission prediction model against the data, and system 400 accumulates the received data in data storage 416. Data storage 416 includes a patient data store 416a, admit data store 416b, and diagnosis data store 416c, in this example. Patient data store 416a includes vital information about the patients, such as age, birth date, residence/location (Zip code), etc. Admit data store 416b includes admission data about the patients, and diagnosis data store 416c includes some or all of the diagnoses associated with the patients. In one particular example, the diagnosis data store includes International Statistical Classification of Diseases and Related Health Problems, $9^{th}$ Revision (ICD-9) codes for each admission and emergency room visit.

After source data is received by system 400, data validation component 408 can provide data validation capabilities for validating the source data. Examples of data validation include: verifying that the admit date listed for the admission is not prior to the patient's birth date, and validating that the diagnosis codes associated with patient diagnoses are valid, as examples. Other data validation could be performed as well.

Once the data is validated, model execution can be performed against the data to obtain the Risk Scores for the newly admitted patients. In one example, the readmission prediction model is implemented on system 400 through a combination of predictive logic 410 and data categorization 412. Data categorization refers to the categorizing of the received data, such as into categories of diagnoses or other patient attributes described above, which can have coefficients attached to them indicating their significance within the model. For instance, diagnosis categories can include, as examples: congestive heart failure, chronic obstructive pulmonary disease, advanced liver disease, diabetes with complication, severe chronic renal failure, Parkinson's disease, leukemia, substance abuse, bipolar conditions, and severe personality disorder, among other diagnostic categories associated with, for instance, higher rates of readmission of a patient. These categories are not mutually exclusive, in that a patient may have more than one of these. In this regard, the patient (by way of the patient data) is flagged as either being within or without each of the particular categories.

Predictive logic 410, which in one example comprises program code including instructions for execution, can be executed to determine the Risk Score of the newly admitted patients based on the source data received for the newly admitted patients and an obtained readmission prediction model. For instance, the data can be run through the regression function derived from the built readmission prediction model. The readmission prediction model is obtained, in one embodiment, from another system that builds the model, which is then transmitted to, or retrieved by, system 400. Alternatively or additionally, system 400 obtains the model by building the model itself using a process described in connection with FIGS. 2 and 6.

In any case, after the predictive logic executes to determine the Risk Scores, the resulting Risk Score for each of the newly admitted patients represented in the source data can be returned to the facility from which the new admit patient data was received as return data.

Figure 5:
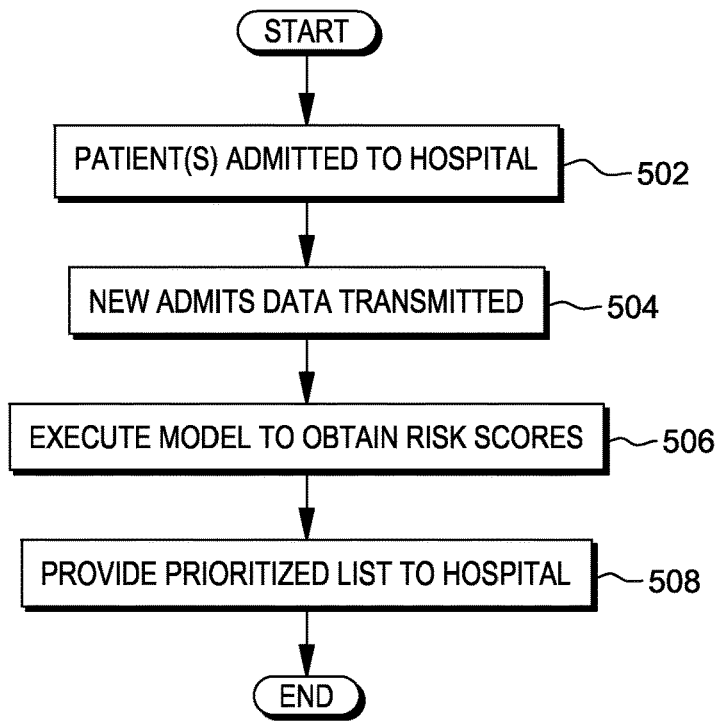
FIG. 5 depicts an overview process for predicting readmission likelihood for newly admitted patients, in accordance with one or more aspects of the invention.

FIG. 5 depicts an overview of a process for predicting readmission likelihood for newly admitted patients, in accordance with one or more aspects of the invention. The process can facilitate a transition management program of a hospital, as an example. The process begins when patients are admitted to a hospital (502). Patient data is collected and transmitted as New Admit data to a server (504). For instance, each morning, a list of new admits and corresponding data on key variables is automatically transmitted, e.g. electronically, to a readmission prediction system/server. A readmission prediction model, built for the particular hospital based on, e.g. prior claims data of the hospital, and therefore calibrated to that particular institution, is then executed to obtain Risk Scores for each of the patients reflected in the new admit data (506). Subsequently, those patients can be ranked on a list by priority, such as their probability of experiencing a potentially preventable readmission. This prioritized list can then be provided to the hospital (508) such as by placing the list in a data store of the hospital, or a data store accessible to the hospital, via a secure website. In one example, a hospital case manager can retrieve the list and work his/her way down the list patient-by-patient, attempting to enroll in a transition management program those patients with highest risk of readmission.

Additionally or alternatively, the predictive information provided to the hospital can be used for discharge management, follow-up activity, clinical decision-making, performance monitoring, and/or payment transformation, as examples, by, for instance, various state entities and/or healthcare organizations or clients thereof.

Figure 6:
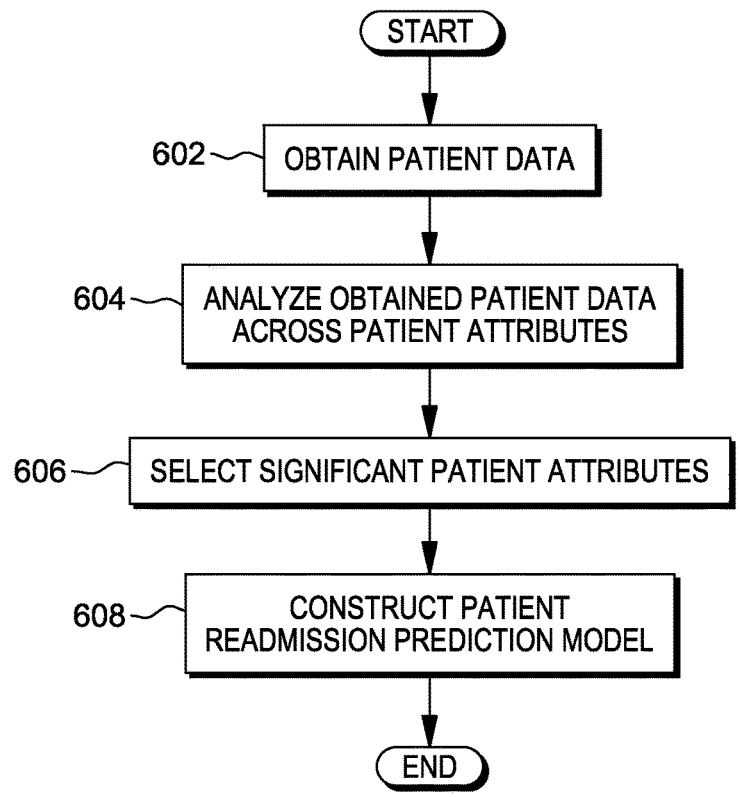
FIG. 6 depicts another example process for building a patient readmission prediction model, in accordance with one or more aspects of the present invention.

Turning now to FIG. 6, another example process for building a patient readmission prediction model is provided. In one example, the process is performed by a data processing system, such as a system described above with reference to FIG. 4. The process begins by obtaining patient data (602). The patient data can be obtained from any number of different sources, such as health care practitioners, organizations, hospitals, providers and/or from health information made available by state or federal officials. In one example, the obtained patient data is tailored to health care claims corresponding to multiple patients and taken over a period of time (such as the past two years) and/or taken across a geographic area (such as a particular Zip code, county, or other defined geographic area). Additionally or alternatively, the data is limited to patient data from one or more particular health care provider(s), such as one or more health care providers to which a newly admitted patient is admitted for care and for which a prediction of readmission is to be made. By using such tailored patient data in building the patient readmission prediction model, the model is calibrated to the one or more health care providers. Similarly, if the patient data is limited to a particular geographic area, the model is calibrated to that particular geographic area (such as providers in that area, or patient-residents of that area). Tailoring the model to the particular institution facilitates improving prediction of potentially preventable readmission of patients attributed to that institution.

Figure 7:
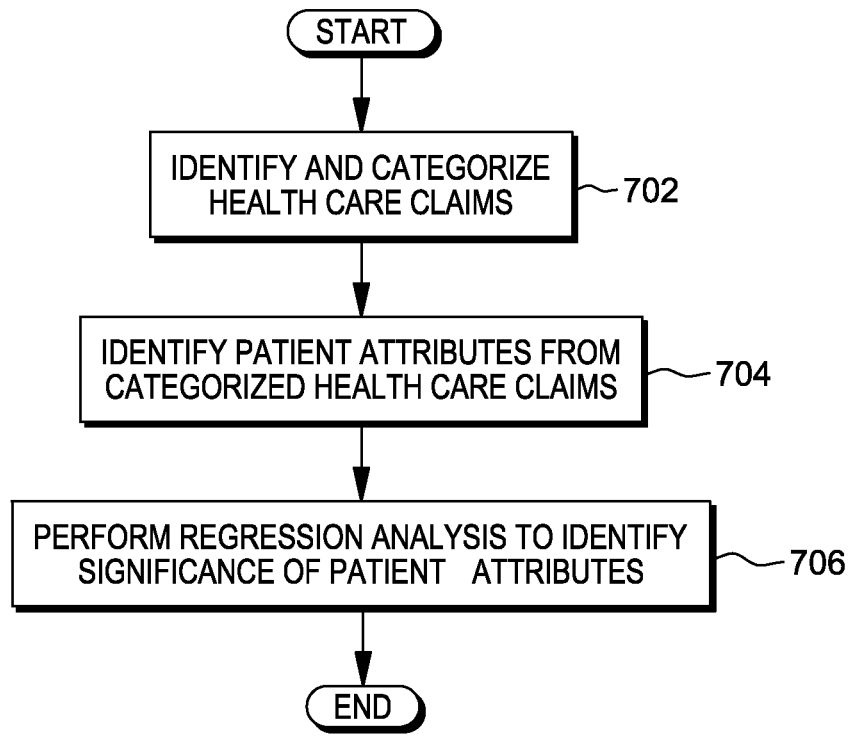
FIG. 7 depicts one example of a process for analyzing obtained patient data across a plurality of patient attributes, in accordance with one or more aspects of the present invention.

Next, the obtained patient data is analyzed across a plurality of patient attributes (604). The analysis determines, for each of these patient attributes, significance of the attribute in predicting potentially preventable patient readmission. FIG. 7 depicts one example of a specific process for analyzing obtained patient data across a plurality of patient attributes, in accordance with one or more aspects of the present invention. The analysis includes first identifying and categorizing each health care claim of the health care claims of the obtained patient data (702). In one example, the health care claims are categorized according to a degree to which each health care claim is considered a potentially preventable readmission. Next, patient attributes are identified from the categorized health care claims 704). Once the patient attributes are identified, statistical analysis can be performed on the attributes to determine their respective significances. For instance, regression analysis, such as a logistic regression (stepwise logistic regression, as a particular example), is performed on the identified patient attributes, and this identifies the significance of each patient attribute in predicting potentially preventable patient readmission (706).

Returning to FIG. 6, based on the analysis from (604), patient attribute(s) are selected based on their identified significance in predicting likelihood of patient readmission (606). The patient readmission prediction model is then constructed (608), i.e. from the multiple selected patient attributes and based on the determined significance for each selected patient attribute of the multiple selected patient attributes. In this manner, a variable is created in the model, and the variable corresponds to a significant patient attribute. The variable has an associated coefficient for that variable, which reflects the variable's relative significance (as compared to other selected variables of the model) in predicting the likelihood of readmission. The variables and coefficients are included in an equation of the patient readmission prediction model.

Figure 8:
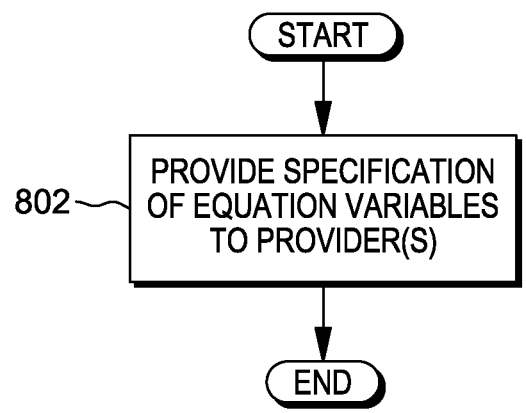
FIG. 8 depicts one example of a process for notifying providers of relevant data for predicting likelihood of potentially preventable patient readmission, in accordance with one or more aspects of the present invention.

Optionally, once the relevant variables are identified (e.g. by the process of FIG. 7), providers can be notified of those variables and/or the relevant New Admit data that those providers are to provide. An example of this is depicted in FIG. 8. In this example, the system (performing the analyzing of FIG. 7 or the building of FIG. 6) provides a specification of readmission prediction model equation variables to the provider(s) of the newly admitted patient data (802). The specification notifies the providers of the type of data used by the model, and therefore that the providers should provide to the system for most accurately predicting readmission likelihood. In response, the data provided by the health care provider(s) to the system is provided based on the specification that they receive of the desired data types for use in the model. Thus, the received patient data includes for at least some of the variables of the equation of the patient readmission prediction model.

The readmission prediction model may be built/rebuilt periodically. For instance, the process of FIG. 6 may be repeated every n number of months, or upon obtaining an updated data set, in order to keep the model up-to-date. Additionally or alternatively, New Admit patient data, which is the data against which the models are applied, may itself be used as source data for building more up-to-date models. In this manner, New Admit patient data that was recently obtained may supplement or augment the other data that is/was used to build the prediction model(s).

Once a patient readmission prediction model is built, it is used to predict the likelihood of a potentially preventable readmission for patients post-discharge from the health care provider. This is done by applying the model against patient data for newly admitted patients. In one example, the model is applied periodically, and against new (different) patient data of newly admitted patients. For instance, the model may be applied daily against a new set of New Admit patient data, such as New Admit patient data for patient admitted during the previous day. In this manner, admitted patient data may be periodically obtained from the health care provider across multiple periods of time (such as daily). The readmission prediction can be repeated, for each of these periods of time, to predict the likelihood of potentially preventable readmission of the patients admitted for care during each of those periods.

Figure 9:
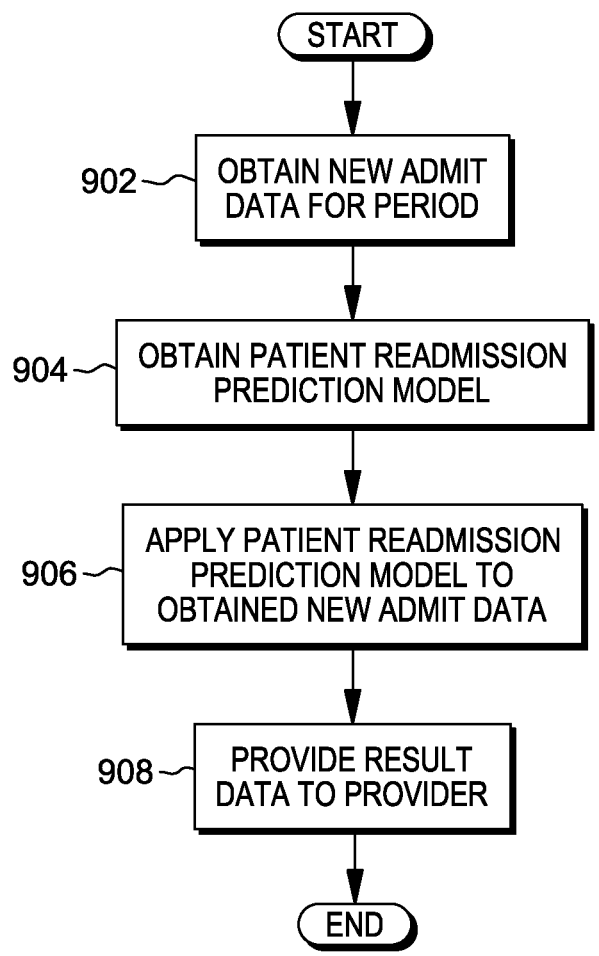
FIG. 9 depicts one example of a process for predicting likelihood of post-discharge, preventable patient readmission, in accordance with one or more aspects of the present invention.

FIG. 9 depicts one example of a process for predicting likelihood of post-discharge, preventable patient readmission, in accordance with one or more aspects of the present invention. In one example, the system of FIG. 4 executes program code to perform the steps of the method. The method begins by obtaining New Admit patient data for a particular period of time (902). The New Admit patient data for a period of time includes patient data for patients admitted to care by the provider during that period of time. Next, a patient readmission prediction model is obtained (904). The patient readmission prediction model is based on a determination of patient attributes that are selected as being meaningful in predicting likelihood of post-discharge, potentially preventable patient readmission. The patient readmission prediction model could be obtained by building the model, such as according to the process of FIG. 6. Additionally or alternatively, the readmission prediction model could be obtained by actively retrieving the model from a remote source, or receiving the model from a remote source. The remote source could be a remote system dedicated to the building of readmission prediction model(s) for one or many clients, as an example.

After obtaining the patient readmission prediction model, the process continues by applying the obtained patient readmission prediction model against the obtained patient data to obtain predictive risk score(s) indicative of the probability of a potentially preventable readmission of the patient(s) post-discharge from the health care provider (906). Thus, a prediction is made for the patients admitted for care by the health care provider about the likelihood of a potentially preventable readmission of the patients post-discharge from the health care provider. Applying the readmission prediction model against the patient data for the admitted patients includes using the equation of the patient readmission prediction model and the provided data to calculate the predictive risk score. For each newly admitted patient reflected in the obtained new admit patient data, that patient's relevant patient data (i.e. data that corresponds to a variable of the equation) is input to the equation, and the system solves the equation to obtain the predictive risk score for that patient. The result is a predictive risk score for each newly admitted patient.

Finally, result data, based on these predictive risk scores, is provided to the health care provider that is the source of the New Admit patient data (i.e. to which the admitted patients were admitted for care) (908). The result data is, in one example, a prioritized list of the newly admitted patients, for instance prioritized by their probability of experiencing a potentially preventable readmission (based on the predictive risk score). This result data can be used by the provider for constructive purposes, such as to facilitate discharge care management intervention or follow-up activity for one or more of the newly admitted patients, or to facilitate clinical decision-making, performance monitoring, or payment transformation, as examples. Alternatively or additionally the result data can be used for any purpose that the provider sees fit.

Described above, and in accordance with aspects of the present invention, is prediction of potentially preventable readmissions, which is more useful than a mere conclusion made in hindsight that a particular admission was a potentially preventable readmission. The prediction is prospective since the variables examined (i.e. those of the built model) predate the later hospitalization. Additionally, the probability of readmission is not for an all-cause readmission, but is instead a probability for readmission that is potentially preventable, and is thus more useful from at least a targeted discharge/follow-up services standpoint. Furthermore, because the patient dataset on which the model is based is for a defined entity (such as an institution, hospital, geographic area, etc.), the particular model used is calibrated to that particular targeted entity. Yet further, the prediction of potentially preventable readmission is, at least in some examples, not disease-specific, in that it examines the total health status of the patient and the patient's demographic factors and predicts the potential for any preventable readmission, not just readmissions associated with a particular disease.

Those having ordinary skill in the art will recognize that aspects of the present invention may be embodied in one or more systems, one or more methods and/or one or more computer program products. In some embodiments, aspects of the present invention may be embodied entirely in hardware, entirely in software (for instance in firmware, resident software, micro-code, etc.), or in a combination of software and hardware aspects that may all generally be referred to herein as a "system" and include circuit(s) and/or module(s).

In some embodiments, aspects of the present invention may take the form of a computer program product embodied in one or more computer readable medium(s). The one or more computer readable medium(s) may have embodied thereon computer readable program code. Various computer readable medium(s) or combinations thereof may be utilized. For instance, the computer readable medium(s) may comprise a computer readable storage medium, examples of which include (but are not limited to) one or more electronic, magnetic, optical, or semiconductor systems, apparatuses, or devices, or any suitable combination of the foregoing. Example computer readable storage medium(s) include, for instance: an electrical connection having one or more wires, a portable computer diskette, a hard disk or mass-storage device, a random access memory (RAM), read-only memory (ROM), and/or erasable-programmable read-only memory such as EPROM or Flash memory, an optical fiber, a portable compact disc read-only memory (CD-ROM), an optical storage device, a magnetic storage device (including a tape device), or any suitable combination of the above. A computer readable storage medium is defined to comprise a tangible medium that can contain or store program code for use by or in connection with an instruction execution system, apparatus, or device, such as a processor. The program code stored in/on the computer readable medium therefore produces an article of manufacture (such as a "computer program product") including program code.

Figure 10:
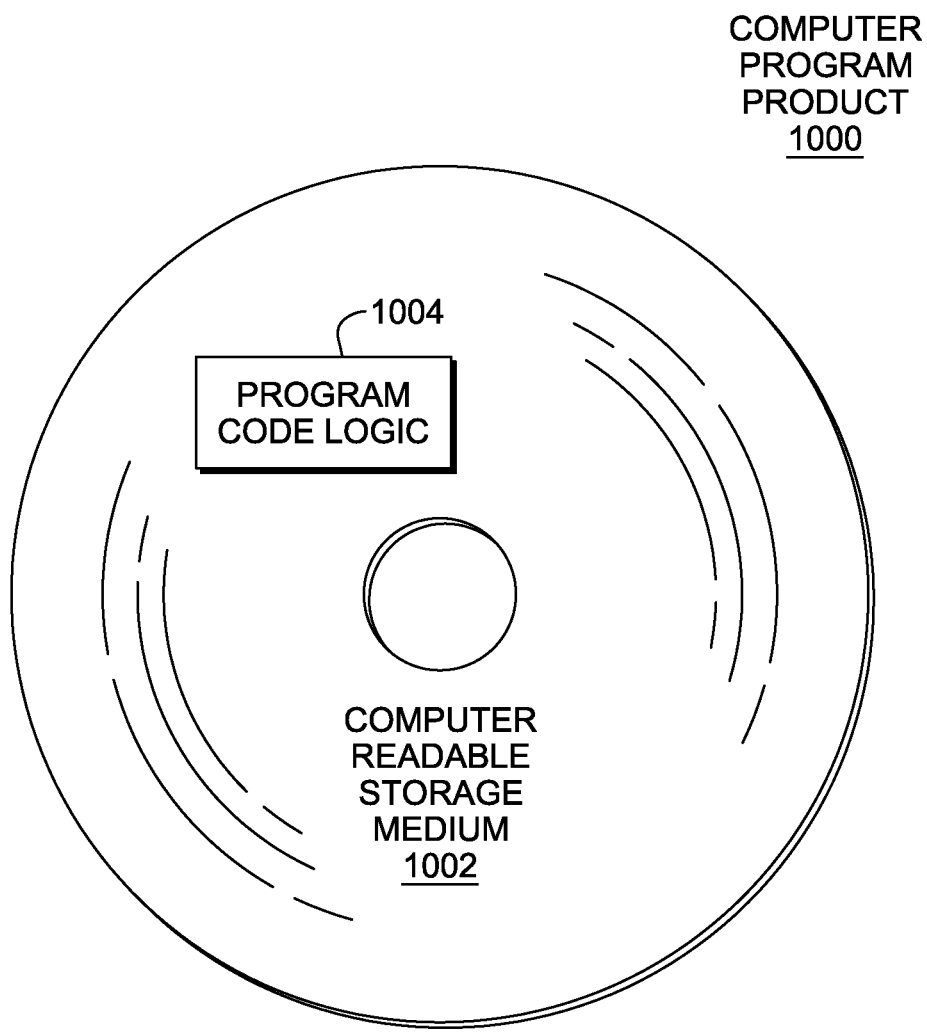
FIG. 10 depicts one embodiment of a computer program product incorporating one or more aspects of the present invention.

Referring now to FIG. 10, in one example, a computer program product 1000 includes, for instance, one or more computer readable media 1002 to store computer readable program code means or logic 1004 thereon to provide and facilitate one or more aspects of the present invention.

Program code contained or stored in/on a computer readable medium can be obtained and executed by a data processing system (computer, computer system, etc. including a component thereof) and/or other devices to cause the data processing system, component thereof, and/or other device to behave/function in a particular manner. The program code can be transmitted using any appropriate medium, including (but not limited to) wireless, wireline, optical fiber, and/or radio-frequency. Program code for carrying out operations to perform, achieve, or facilitate aspects of the present invention may be written in one or more programming languages. In some embodiments, the programming language(s) include object-oriented and/or procedural programming languages such as C, C++, C#, Java, etc. Program code may execute entirely on the user's computer, entirely remote from the user's computer, or a combination of partly on the user's computer and partly on a remote computer. In some embodiments, a user's computer and a remote computer are in communication via a network such as a local area network (LAN) or a wide area network (WAN), and/or via an external computer (for example, through the Internet using an Internet Service Provider).

In one example, program code includes one or more program instructions obtained for execution by one or more processors. Computer program instructions may be provided to one or more processors of, e.g., one or more data processing system, to produce a machine, such that the program instructions, when executed by the one or more processors, perform, achieve, or facilitate aspects of the present invention, such as actions or functions described in flowcharts and/or block diagrams described herein. Thus, each block, or combinations of blocks, of the flowchart illustrations and/or block diagrams depicted and described herein can be implemented, in some embodiments, by computer program instructions.

The flowcharts and block diagrams depicted and described with reference to the Figures illustrate the architecture, functionality, and operation of possible embodiments of systems, methods and/or computer program products according to aspects of the present invention. These flowchart illustrations and/or block diagrams could, therefore, be of methods, apparatuses (systems), and/or computer program products according to aspects of the present invention.

In some embodiments, as noted above, each block in a flowchart or block diagram may represent a module, segment, or portion of code, which comprises one or more executable instructions for implementing the specified behaviors and/or logical functions of the block. Those having ordinary skill in the art will appreciate that behaviors/functions specified or performed by a block may occur in a different order than depicted and/or described, or may occur simultaneous to, or partially/wholly concurrent with, one or more other blocks. Two blocks shown in succession may, in fact, be executed substantially concurrently, or the blocks may sometimes be executed in the reverse order. Additionally, each block of the block diagrams and/or flowchart illustrations, and combinations of blocks in the block diagrams and/or flowchart illustrations, can be implemented wholly by special-purpose hardware-based systems, or in combination with computer instructions, that perform the behaviors/functions specified by a block or entire block diagram or flowchart.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A method comprising:
   building a patient readmission prediction model, the patient readmission prediction model based on a determination of patient attributes selected as being meaningful in predicting likelihood of post-discharge, potentially preventable patient readmission, wherein building the patient readmission prediction model comprises:

receiving patient data corresponding to multiple patients to which at least one health care provider provides health care services, the at least one health care provider comprising the health care provider to which the admitted patient is admitted for care;

analyzing the received patient data across a plurality of patient attributes using statistical regression to determine statistical significance, for each patient attribute of the plurality of patient attributes, in predicting potentially preventable patient readmission;

selecting, from the plurality of patient attributes, multiple patient attributes determined to be statistically significant in predicting potentially preventable patient readmission using stepwise regression analysis employing at least one of significance level for selection (SLS) and significance level for elimination (SLE) to determine selection or exclusion of each statistically significant patient attribute; and constructing the patient readmission prediction model from the multiple selected patient attributes and based on the determined statistical significance for each selected patient attribute of the multiple selected patient attributes, wherein a variable and coefficient for that variable are determined for each patient attribute of the multiple selected patient attributes, and included in an equation of the patient readmission prediction model, the equation including multiple variables and multiple coefficients wherein each variable corresponds to a patient attribute of the multiple selected patient attributes and the coefficient for that variable indicates a significance of that variable in predicting potentially preventable readmission of the patient;

obtaining, by a model execution server, the patient readmission prediction model;

sending, by the model execution server via a communication network, a request for a transmission of a first determined variable corresponding to a first selected patient attribute;

receiving, by the model execution server, from a health care facility via the communication network, a data feed containing patient data comprising, for a plurality of patients admitted to the health care facility, the first determined variable for each of the plurality of admitted patients;

applying, by the model execution server, the patient readmission prediction model against the data feed to obtain a predictive risk score for each of the plurality of admitted patients, the predictive risk score being indicative of the probability of a potentially preventable readmission of the patient post-discharge from the health care facility;

generating, by the model execution server, a prioritized list of patients based on the obtained predictive risk scores; and transmitting, by the model execution server via the communication network, the prioritized list to the health care facility.

2. The method of claim 1, wherein the received patient data corresponding to multiple patients is data associated with the health care facility, wherein building the patient readmission prediction model based on the received patient data corresponding to multiple patients calibrates the patient readmission prediction model to the at least one health care facility, wherein the calibrating facilitates improving prediction of potentially preventable readmission of patients admitted to the health care facility.

3. The method of claim 1, wherein the received patient data corresponding to the multiple patients comprises health care claims data corresponding to health care claims by the multiple patients, the health care claims taken over a period of time or taken across a geographic area.

4. The method of claim 3, wherein analyzing the received patient data comprises:

identifying and categorizing each health care claim of the health care claims according to a degree to which each health care claim is considered a potentially preventable readmission;

identifying the plurality of patient attributes from the health care claims; and performing a logistic regression on the plurality of patient attributes, wherein the logistic regression identifies the significance of each patient attribute of the plurality of patient attributes in predicting potentially preventable patient readmission, and wherein the multiple selected patient attributes are selected based on the identified significance of each patient attribute.

5. The method of claim 1, wherein the patient data for the admitted patient is obtained from the health care provider to which the admitted patient is admitted for care, and wherein the patient data for the admitted patient comprises data for at least some variables of the multiple variables of the equation of the patient readmission prediction model.

6. The method of claim 5, wherein the method further comprises providing, to the health care facility, a specification of the multiple variables included in the equation of the patient readmission prediction model, wherein the data feed is based on the provided specification.

7. The method of claim 5, wherein applying the patient readmission prediction model against the data feed comprises using the equation of the patient readmission prediction model and the provided determined variables in the data feed to calculate the predictive risk score.

8. The method of claim 1, wherein the multiple selected patient attributes include at least one of: one or more patient morbidity characteristics, service utilization history, social economic status, or clinical lab values.

9. The method of claim 1, wherein the method further comprises providing result data, based on the predictive risk score, to the health care provider to which the admitted patient is admitted for care, wherein the provided result data facilitates at least one of: discharge care management intervention or follow-up activity for the patient by the health care provider, clinical decision-making, performance monitoring, or payment transformation.

10. The method of claim 1, wherein the prioritized list contains a plurality of predictive risk scores.

11. The method of claim 10, further comprising providing, to the health care facility via the communication network, result data based on the plurality of predictive risk scores, wherein the provided result data facilitates prioritizing at least one of: discharge care management intervention or follow-up activity for the plurality of admitted patients by the health care provider.

12. The method of claim 1, wherein the data feed is periodically received from the health care facility for multiple periods of time, wherein the data feed for a period of time of the multiple periods of time comprises the first determined variable for patients admitted for care by the health care facility during that period of time, and wherein the method further comprises:

applying the patient readmission prediction model against the data feed for that period of time; and transmitting, to the health care facility, result data based on a predictive risk score for each of the patients admitted for care by the health care provider during that period of time, wherein the result data facilitates prioritizing at least one of: discharge care management intervention or follow-up activity by the health care provider, for a plurality of patients admitted for care by the health care facility.

13. The method of claim 1, wherein applying the patient readmission prediction model is performed prior to discharge of the plurality of patients admitted to the health care facility.

14. A patient readmission prediction system comprising:
a model execution server comprising:
a memory and a processor in communication with the memory, the memory storing:
patient data for a plurality of newly admitted patients admitted to a health care provider, the patient data being received from the health care provider via a communication network; and
a patient readmission prediction model based on a determination of patient attributes selected as being meaningful in predicting likelihood of post-discharge, potentially preventable patient readmission, the patient readmission prediction model built by a process comprising:
receiving patient claims data from the health care provider via the communication network, the patient claims data corresponding to multiple patients to which the health care provider provides health care services;
analyzing the patient claims data across a plurality of patient attributes using statistical regression to determine statistical significance, for each patient attribute of the plurality of patient attributes, in predicting potentially preventable patient readmission;
selecting, from among the plurality of patient attributes, multiple patient attributes determined to be statistically significant in predicting potentially preventable patient readmission using stepwise regression analysis employing at least one of significance level for selection (SLS) and significance level for elimination (SLE) to determine selection or exclusion of each statistically significant patient attribute;
constructing the patient readmission prediction model from the multiple selected patient attributes and based on the determined statistical significance for each selected patient attribute of the multiple selected patient attributes, wherein a variable and coefficient for that variable are determined for each patient attribute of the multiple selected patient attributes, and included in an equation of the patient readmission prediction model, the equation including multiple variables and multiple coefficients wherein each variable corresponds to a patient attribute of the multiple selected patient attributes and the coefficient for that variable indicates a significance of that variable in predicting potentially preventable readmission of the patient; and
program code comprising instructions that, when executed, cause the processor to:

send, via the communication network, a request for a transmission of a first determined variable corresponding to a first selected patient attribute;

receive, from a health care facility via the communication network, a data feed containing patient data comprising, for a plurality of patients admitted to the health care facility, the first determined variable for each of the plurality of admitted patients;

apply the patient readmission prediction model against the data feed received from the health care facility to obtain a predictive risk score indicative of the probability of a potentially preventable readmission for each newly admitted patient post-discharge from the health care facility;

generate a prioritized list of patients based on the obtained predictive risk scores; and transmit the prioritized list to the health care facility via the communication network.

15. The system of claim 14, wherein additional patient data is periodically obtained from the health care provider for multiple periods of time, wherein the additional patient data for a period of time of the multiple periods of time comprises patient data for patients admitted for care by the health care provider during that period of time, and wherein the program code further comprises instructions that, when executed, cause the processor to:
for each period of time of the multiple periods of time, apply the patient readmission prediction model against the patient data received for that period of time; and
transmit, to the health care provider, result data based on the predictive risk score, wherein the result data facilitates prioritizing at least one of:
discharge care management intervention, and
follow-up activity by the health care provider, for a plurality of patients admitted for care by the health care provider.

16. The system of claim 14, the memory further storing admission data and diagnosis data for the plurality of newly admitted patients, the admission data and diagnosis data being received from the health care provider via the communication network.

17. A patient readmission prediction system comprising:
a model execution server comprising:
a memory and a processor in communication with the memory, the memory storing:
a data feed containing patient data for a plurality of newly admitted patients admitted to a health care facility, the data feed being received from the health care provider via a communication network; and
a patient readmission prediction model based on a determination of patient attributes selected as being meaningful in predicting likelihood of post-discharge, potentially preventable patient readmission, the patient readmission prediction model built by a process comprising:
receiving patient claims data from a health care provider via the communication network, the patient claims data corresponding to multiple patients to whom the health care provider provides health care services,
analyzing the patient claims data across a plurality of patient attributes using statistical regression to determine statistical significance, for each patient attribute of the plurality of patient attributes, in predicting potentially preventable patient readmission, and selecting, from among the plurality of patient attributes, multiple patient attributes determined to be statistically significant in predicting potentially preventable patient readmission; and program code comprising instructions that, when executed, cause the processor to:
  apply the patient readmission prediction model against the data feed received from the health care facility for each newly admitted patient,
  determine a predictive risk score indicative of the probability of a potentially preventable readmission of each newly admitted patient post-discharge from the health care provider,
  generate a prioritized list of patients based on the determined predictive risk scores; and
  transmit the prioritized list to the health care facility.

18. The patient readmission prediction system of claim 17, further comprising a data store accessible by the health care facility, the data store being in communication with the model execution server via the communication network,
  wherein the program code of the model execution server further comprises instructions that, when executed, cause the processor to transmit the determined predictive risk scores and the data feed to the data store.

* * * * *